United States Patent
Lowman et al.

(10) Patent No.: US 10,507,264 B1
(45) Date of Patent: Dec. 17, 2019

(54) CROSS-LINKED HYDROGELS AND METHOD OF MAKING THE SAME

(71) Applicant: Regeltec, Inc., Baltimore, MD (US)

(72) Inventors: Anthony Lowman, Clarksboro, NJ (US); Erik Brewer, Conshohocken, PA (US); Nigel Gordon Smith, North Walsham (GB)

(73) Assignee: REGELTEC, INC., Baltimore, MD (US)

( * ) Notice: Subject to any disclaimer, the term of this patent is extended or adjusted under 35 U.S.C. 154(b) by 0 days.

(21) Appl. No.: 16/241,510

(22) Filed: Jan. 7, 2019

(51) Int. Cl.
| | |
|---|---|
| *A61L 27/26* | (2006.01) |
| *A61L 27/02* | (2006.01) |
| *A61L 27/52* | (2006.01) |
| *C08L 29/04* | (2006.01) |
| *C08L 39/06* | (2006.01) |
| *C08L 71/02* | (2006.01) |

(52) U.S. Cl.
CPC ............. *A61L 27/26* (2013.01); *A61L 27/025* (2013.01); *A61L 27/52* (2013.01); *A61L 2400/06* (2013.01); *A61L 2430/34* (2013.01); *A61L 2430/38* (2013.01); *C08L 29/04* (2013.01); *C08L 39/06* (2013.01); *C08L 71/02* (2013.01)

(58) Field of Classification Search
CPC ........ A61L 27/26; A61L 27/025; A61L 27/52; A61L 2430/38; A61L 2400/06; A61L 2430/34; C08L 29/04; C08L 39/06; C08L 71/02
See application file for complete search history.

(56) References Cited

U.S. PATENT DOCUMENTS

| | | | |
|---|---|---|---|
| 7,850,730 | B2 | 12/2010 | Vresilovic et al. |
| 8,366,778 | B2 | 2/2013 | Kita et al. |
| 8,475,532 | B2 | 7/2013 | Vresilovic et al. |
| 8,617,519 | B2 | 12/2013 | Binetti et al. |
| 8,703,157 | B2 | 4/2014 | Kita et al. |
| 9,078,953 | B2 | 7/2015 | Kita et al. |
| 2006/0122704 | A1 | 6/2006 | Vresilovic et al. |
| 2006/0276802 | A1 | 12/2006 | Vresilovic et al. |
| 2010/0272672 | A1 | 10/2010 | Kita et al. |
| 2010/0286786 | A1 | 11/2010 | Kita et al. |
| 2011/0270400 | A1 | 11/2011 | Kita et al. |

(Continued)

FOREIGN PATENT DOCUMENTS

| | | |
|---|---|---|
| WO | WO-2006105190 A2 | 10/2006 |
| WO | WO-2009079507 A2 | 6/2009 |

(Continued)

OTHER PUBLICATIONS

Binetti, Development and Characterization of a Chemically Cross-linked Polyvinyl Alcohol/Polyethylene Glycol Hydrogel for Injectable Nucleus Pulposus Replacement, May 2013, Thesis—Drexel University, 289 pages. (Year: 2013).*

*Primary Examiner* — Trevor Love
(74) *Attorney, Agent, or Firm* — Cooley LLP

(57) ABSTRACT

The present disclosure relates to hydrogels and their use for repairing or supplementing body tissue. The hydrogels are capable of safe injection into patients through fine gauge needles and are suitable for repairing or supplementing the nucleus pulposus of an intervertebral disc. Methods of manufacturing and methods of using the hydrogels of the present disclosure to repair or replace tissues are also disclosed.

16 Claims, 5 Drawing Sheets

(56) References Cited

U.S. PATENT DOCUMENTS

2011/0276140 A1 11/2011 Vresilovic et al.
2013/0012913 A1 1/2013 Binetti et al.

FOREIGN PATENT DOCUMENTS

WO    WO-2009089526 A2    7/2009
WO    WO-2009146331 A1   12/2009
WO    WO-2013006237 A1    1/2013

* cited by examiner

CROSS-LINKED HYDROGELS AND METHOD OF MAKING THE SAME

FIELD OF THE DISCLOSURE

The present disclosure relates to hydrogels and their use for repairing or supplementing body tissue. The hydrogels are capable of safe injection into patients through fine gauge needles and are suitable for repairing or supplementing the nucleus pulposus of an intervertebral disc.

BACKGROUND OF THE INVENTION

The human intervertebral disc is comprised of two major structures, an outer or peripheral tendinous structure, and an inner gelatinous nucleus pulposus located in a generally central region. Degeneration of the nucleus pulposus, which is typically associated with natural aging, may lead to disc degradation and loss of function.

Many patients experience chronic back pain caused by injury or age-related degeneration of an intervertebral disc. Current treatments range from bed rest to invasive surgical procedures, including discectomy, spinal fusion and total disc replacement.

Replacement or supplementation of the nucleus pulposus can relieve pain, restore healthy physiologic function to the disc and/or prevent additional wear or deterioration of the annulus. Currently, few minimally invasive techniques or materials exist for supplementation or replacement of the nucleus pulposus of a spinal disc into a selected site of a mammal. Even fewer techniques or materials provide the physiological/mechanical properties to restore the damaged disc to its full capacity.

Existing hydrogel technologies for supplementing or repairing the nucleus pulposus require the injection of pre-heated hydrogels through a large gauge needle into the intervertebral space. The resulting punctures may cause severe patient discomfort and provide an opening through which the resulting implant may be expelled. Thus, there is a need for hydrogels that permit injection via fine gauge needles (15 gauge and finer) while providing tissue implants that possess the required mechanical properties to support an intervertebral disc.

SUMMARY OF THE INVENTION

In one aspect, the present disclosure provides hydrogels that are suitable for safe injection into the tissue of a living patient in need of repair or supplement through fine gauge needles (e.g., a 17-gauge needle) to provide tissue implants with mechanical properties that are suitable for the intended use. In some embodiments, the hydrogels are suitable for the repair and/or supplement of the nucleus pulposus of a patient in need thereof.

In some embodiments, the present disclosure provides hydrogels comprising: at least one polymer; and a solvent, wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa.

In some embodiments, the present disclosure provides hydrogels comprising: at least one polymer; and a solvent, wherein at a temperature of about 65° C. the hydrogel is capable of safe injection into the nucleus of an intervertebral disc of a living patient through a 16 cm length, 17 gauge needle to provide a tissue implant having a mechanical modulus of between about 0.1 to 5.0 MPa.

In certain embodiments, the at least one polymer is selected from the group consisting of polyvinyl alcohol, polyvinylpyrrolidone and polyethylene glycol. In some embodiments, the hydrogel polymers comprise a mixture of polyvinyl alcohol, polyvinylpyrrolidone and polyethylene glycol. In some embodiments, the hydrogel polymers consist essentially of polyvinyl alcohol, polyvinylpyrrolidone and polyethylene glycol.

In some embodiments, the hydrogels of the present disclosure comprise
  (a) about 12 wt. % to about 22 wt. % of polyvinyl alcohol;
  (b) about 0.12 wt. % to about 0.22 wt. % of polyvinylpyrrolidone; and
  (c) about 12 wt. % to about 22 wt. % of polyethylene glycol.

In one aspect, the present disclosure provides kits comprising a hydrogel of the present disclosure packaged in a suitable container. In some embodiments, the kits further comprise a hydrogel delivery device. In particular embodiments, the hydrogel delivery device is the device shown in FIG. 1.

In one aspect, the present disclosure provides methods of making the hydrogels described herein. In some embodiments, the present disclosure provides hydrogels that are prepared according to the methods described herein (i.e., product-by-process).

In one aspect, the present disclosure provides tissue implants having a mechanical modulus of between about 0.1 to 5.0 MPa that are prepared by injecting the hydrogels of the present disclosure into the tissue of a patient in need thereof. In some embodiments, the tissue implants of the present disclosure have a mechanical modulus of about 0.1 MPa to about 1.0 MPa.

In one aspect, the present disclosure provides methods of using the hydrogels described herein to repair and/or supplement the tissue of a patient in need thereof. In some embodiments, present disclosure provides methods of using the hydrogels to repair and/or supplement the nucleus pulposus of a patient in need thereof.

BRIEF DESCRIPTION OF THE DRAWINGS

The accompanying drawings, which are incorporated herein and constitute part of this specification, illustrate embodiments of the invention, and, together with the general description given above and the detailed description given below, serve to explain the features of the invention. In the drawings.

DEFINITIONS

Figure 1:
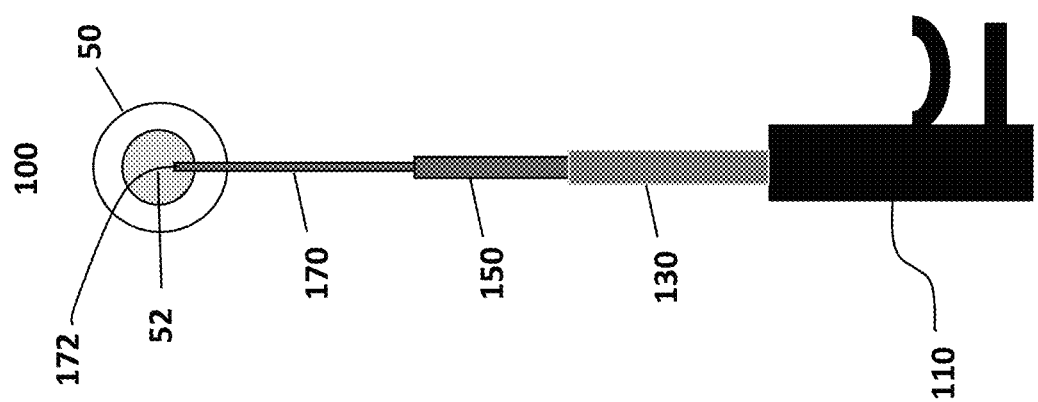
FIG. 1 is a top plan view of a hydrogel delivery device that may be used to inject the hydrogels of the present disclosure into an intervertebral disc to repair or supplement a nucleus pulposus.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The terms "effective amount" and "therapeutically effective amount" are used interchangeably in this disclosure and refer to an amount of a hydrogel, that when injected into a patient's tissue, is capable of forming a tissue implant that in turn performs the intended result. For example, an effective amount of the hydrogel of the present disclosure is that amount that is required to reduce at least one symptom of a patient who receives the hydrogel injection. The actual amount that comprises the "effective amount" or "therapeutically effective amount" will vary depending on a number of conditions including, but not limited to, the area where the hydrogel is injected, the severity of the disorder, the size and health of the patient. A skilled medical practitioner can readily determine the appropriate amount using methods known in the medical arts.

The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral" and related words and/or phrases designate preferred positions and orientations in the human body to which reference is made and are not meant to be limiting. All percentages, unless otherwise indicated, are on a weight to weight (wt./wt.) basis. The terminology includes the above-listed words, derivatives thereof and words of similar import.

DETAILED DESCRIPTION

Certain chemically cross-linked and non-chemically cross-linked hydrogels are suitable for nucleus pulposus replacement and supplementation to repair the intervertebral disc as well as other biomedical applications.

U.S. Pat. Nos. 7,214,245 and 8,703,157 (which are hereby incorporated by reference in their entireties) in combination disclose hydrogels and biomaterials comprising non-chemically cross-linked polymers for repairing the nucleus pulposus and other biomedical applications. The hydrogels described in these references can be applied as solids or, alternatively, as viscous fluids that when injected into a patient form tissue implants with mechanical properties that are applicable for the nucleus pulposus and other structural systems. However, as shown in the Examples, the hydrogels described in U.S. Pat. No. 8,703,157 (the '157 Patent) are injected at very high temperature (about 95° C.) and use relatively large gauge needles (2.5 mm ID or ~10-11G) (see Example 11 of the '157 Patent).

U.S. Pat. No. 8,617,519 (the '519 Patent) discloses chemically cross-linked hydrogels that are said to be flowable when heated above the melting temperature and provide an elastic solid at physiological temperature. However, the '519 Patent does not exemplify the injection of the hydrogels through fine gauge needles, and the viscosity measurements that the Applicants rely on to support the injectability of the hydrogels were determined at very high temperature (about 95° C., see Examples 4 and 5 of the '519 Patent).

Thus, current technologies are limited in their application since their injection requires very high temperature and/or large gauge needles. The use of large gauge needles is particularly problematic in the repair of the nucleus pulposus since the resulting tissue implant may leak out of the disc through the needle borehole after injection.

Accordingly, there is a need for hydrogels that permit injection via fine gauge needles (15 gauge and finer) while providing tissue implants that possess the required mechanical properties to support an intervertebral disc.

Hydrogels and Kits:

In one aspect, the present disclosure provides hydrogels that are capable of safe injection through a fine gauge needle (smaller than 15 gauge, e.g., 17 or 19 gauge) into a living patient and, upon injection, form tissue implants that are suitable as biomaterials. In particular, at temperatures and pressures that are safe for injection into a living patient (for example, for the repair or supplementation of the nucleus pulposus about 65° C. and about 60 p.s.i. to about 120 p.s.i.), the hydrogels of the present disclosure form an injectable composition that when injected into a patient in need thereof solidifies in situ to form a suitable hydrogel tissue implant.

The hydrogels of the present disclosure are well suited for repairing a damaged intervertebral disc. The hydrogels are useful as a full or partial nucleus pulposus replacement or supplementation, as well as for repairing defects, tears or fissures in the disc annulus.

In some embodiments, the hydrogels of the present disclosure are characterized on the basis of their unique functional properties. The hydrogels of the present disclosure are capable of injection through fine gauge needles into a living patient's tissue under temperature and pressure conditions that are safe for use in surgical procedures. As used herein, the phrase "capable of safe injection into a living patient's tissue" is used to functionally describe some embodiments of the hydrogels of the present disclosure and means that the hydrogel may be injected into a patient in need thereof under temperature and pressure conditions that do not cause substantial damage to the tissue surrounding the injection site. The safe injection pressure and temperature will depend in part on the tissue that the hydrogel is injected into and may be determined by those of skill in the art.

As described herein, the pressure during an injection of a hydrogel of the present disclosure is described by the injection pressure or the backpressure. As used herein "injection pressure" is the pressure on the syringe plunger that is needed to transfer the hydrogel of the present disclosure through a particular delivery system (e.g., a 17-gauge needle of defined length) at a particular injection rate (e.g., 1.0 cc per minute) and is determined by delivering the hydrogel through the open system (i.e., the hydrogel is passed from the syringe, through the delivery system and into an open space). As used herein "backpressure" is the pressure measured as a hydrogel of the present disclosure is delivered through a particular delivery system (e.g., a 17-gauge needle of defined length) at a particular injection rate (e.g., 1.0 cc per minute) into a closed system (e.g., the intervertebral space). Backpressure increases during the injection as the hydrogel fills the space into which it is injected.

Methods of measuring injection pressure and backpressure are known to those skilled in the art. In some embodiments of the present disclosure, injection pressure is measured by placing a pressure gauge on the plunger of the hydrogel-containing syringe during the injection to record the injection pressure. In some embodiments of the present disclosure, backpressure is measured by placing a 3-way connector between the hydrogel-containing syringe, the cavity into which the hydrogel is injected (e.g., the intervertebral space) and a pressure gauge to record the backpressure.

In some embodiments, the present disclosure provides a hydrogel, comprising: at least one polymer; and a solvent, wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa. In certain embodiments, the at least one polymer is a mixture of polyvinyl alcohol (PVA), polyvinylpyrrolidone (PVP) and polyethylene glycol (PEG). In some embodiments, the hydrogel does not contain a chemically cross-linked polymer.

In some embodiments, the present disclosure provides a hydrogel that is capable of safe injection into the nucleus of an intervertebral disc under injection conditions (e.g., backpressure and temperature) that do not result in endplate damage or promote a herniation through weakness in the annulus fibrosus. In some embodiments, the hydrogel is capable of injection into the nucleus of an intervertebral disc into a living patient through a 16 cm length, 17 gauge needle at a rate of at least 1.0 cc per minute to provide a tissue implant having a mechanical modulus of between about 0.1 to 5.0 MPa, wherein the backpressure during the injection is from about 35 p.s.i. to about 400 p.s.i., including about 40 p.s.i., about 50 p.s.i., about 60 p.s.i., about 70 p.s.i., about 80 p.s.i., about 90 p.s.i., about 100 p.s.i., about 110 p.s.i., about 120 p.s.i., about 130 p.s.i., about 140 p.s.i., about 150 p.s.i., about 160 p.s.i., about 170 p.s.i., about 180 p.s.i., about 190 p.s.i., about 200 p.s.i., about 210 p.s.i., about 220 p.s.i., about 230 p.s.i., about 240 p.s.i., about 250 p.s.i., about 260 p.s.i., about 270 p.s.i., about 280 p.s.i., about 290 p.s.i., about 300 p.s.i., about 310 p.s.i., about 320 p.s.i., about 330 p.s.i., about 340 p.s.i., about 350 p.s.i., about 360 p.s.i., about 370 p.s.i., about 380 p.s.i., and about 390 p.s.i., and all ranges there in between. In certain embodiments, hydrogel is capable of injection into the nucleus of an intervertebral disc into a living patient through a 16 cm length, 17 gauge needle at a rate of at least 1.0 cc per minute to provide a tissue implant having a mechanical modulus of between about 0.1 to 5.0 MPa, wherein the backpressure during the injection is from about 60 p.s.i. to about 200 p.s.i.

In some embodiments, the hydrogel is capable of injection into the nucleus of an intervertebral disc into a living patient through a 16 cm length, 17 gauge needle at a rate of at least 1.0 cc per minute to provide a tissue implant having a mechanical modulus of between about 0.1 to 5.0 MPa, wherein the maximum backpressure during the injection is less than about 60 p.s.i., about 70 p.s.i., about 80 p.s.i., about 90 p.s.i., about 100 p.s.i., about 110 p.s.i., about 120 p.s.i., about 130 p.s.i., about 140 p.s.i., about 150 p.s.i., about 160 p.s.i., about 170 p.s.i., about 180 p.s.i., about 190 p.s.i., about 200 p.s.i., about 210 p.s.i., about 220 p.s.i., about 230 p.s.i., about 240 p.s.i., about 250 p.s.i., about 260 p.s.i., about 270 p.s.i., about 280 p.s.i., about 290 p.s.i., about 300 p.s.i., about 310 p.s.i., about 320 p.s.i., about 330 p.s.i., about 340 p.s.i., about 350 p.s.i., about 360 p.s.i., about 370 p.s.i., about 380 p.s.i., about 390 p.s.i., and about 400 p.s.i. In certain embodiments, hydrogel is capable of injection into the nucleus of an intervertebral disc into a living patient through a 16 cm length, 17 gauge needle at a rate of at least 1.0 cc per minute to provide a tissue implant having a mechanical modulus of between about 0.1 to 5.0 MPa, wherein the maximum backpressure during the injection is less than about 250 p.s.i. In certain embodiments, hydrogel is capable of injection into the nucleus of an intervertebral disc into a living patient through a 16 cm length, 17 gauge needle at a rate of at least 1.0 cc per minute to provide a tissue implant having a mechanical modulus of between about 0.1 to 5.0 MPa, wherein the maximum backpressure during the injection is less than about 200 p.s.i.

In some embodiments, the hydrogels of the present disclosure are described on the basis of the needle gauge that the hydrogel at a temperature of about 65° C. is capable of injection through using a 16-cm length needle. In some embodiments, the needle gauge is about 15 gauge to about 21 gauge, including about 16 gauge, about 17 gauge, about 18 gauge, about 19 gauge, about 20 gauge and about 21 gauge and all ranges there in between. In certain embodiments, the needle gauge is about 17 gauge to about 19 gauge. In some embodiments, the needle gauge is about 15 gauge, about 16 gauge, about 17 gauge, about 18 gauge, about 19 gauge, about 20 gauge and about 21 gauge. In certain embodiments, the needle gauge is about 18 gauge. In certain embodiments, the needle gauge is about 17 gauge. In certain embodiments, the needle is a 152 mm Tuohy epidural needle.

In some embodiments, the hydrogels of the present disclosure are described on the basis of their viscosity at a temperature of about 65° C. In some embodiments, the viscosity of the hydrogel at a temperature of about 65° C. is about 5 Pascal seconds (Pa·s) to about 70 Pa·s, including about 10 Pa·s, about 15 Pa·s, about 20 Pa·s, about 25 Pa·s, about 30 Pa·s, about 35 Pa·s, about 40 Pa·s, about 45 Pa·s, about 50 Pa·s, about 55 Pa·s, about 60 Pa·s, and about 65 Pa·s, and all ranges there in between. In certain embodiments, the viscosity of the hydrogel at a temperature of about 65° C. is about 10 Pa·s to about 60 Pa·s. In some embodiments, the viscosity of the hydrogel at a temperature of about 65° C. is about 5 Pa·s, about 10 Pa·s, about 15 Pa·s, about 20 Pa·s, about 25 Pa·s, about 30 Pa·s, about 35 Pa·s, about 40 Pa·s, about 45 Pa·s, about 50 Pa·s, about 55 Pa·s, about 60 Pa·s, about 65 Pa·s, or about 70 Pa·s. In some embodiments, the viscosity of the hydrogel at a temperature of about 65° C. is about 10 Pa·s.

In some embodiments, the hydrogels of the present disclosure are described on the basis of the injection rate at which they may be injected through a 16 cm length, 17 gauge needle when the temperature of the composition is about 65° C. In some embodiments, the injection rate of the hydrogel is greater than about 1.0 cc/min. In some embodiments, the injection rate of the hydrogel is greater than about 1.5 cc/min. In some embodiments, the injection rate of the hydrogel is greater than about 2.0 cc/min. In some embodiments, the injection rate of the hydrogel is greater than about 2.5 cc/min. In some embodiments, the injection rate of the hydrogel is greater than about 3.0 cc/min. In some embodiments, the injection rate of the hydrogel is greater than about 3.5 cc/min. In some embodiments, the injection rate of the hydrogel is greater than about 4.0 cc/min. In some embodiments, the injection rate of the hydrogel is greater than about 4.5 cc/min. In some embodiments, the injection rate of the hydrogel is greater than about 5.0 cc/min. In some embodiments, the injection rate of the hydrogel is greater than about 5.5 cc/min. In some embodiments, the injection rate of the hydrogel is greater than about 6.0 cc/min.

In some embodiments, the hydrogels of the present disclosure are described on the basis of the injection temperature at which the composition may be injected through a 16 cm length, 17 gauge needle. In some embodiments, the injection temperature is about 40° C. to about 90° C., including about 50° C., about 55° C., about 60° C., about 65° C., about 70° C., about 75° C., about 80° C., and about 85° C., and all ranges there in between. In certain embodiments, the injection temperature is about 45° C. to about 90° C. In certain embodiments, the injection temperature is about 55° C. to about 70° C. In some embodiments, the injection temperature is about 45° C., about 50° C., about 55° C., about 60° C., about 65° C., about 70° C., about 75° C., about 80° C., about 85° C. or about 90° C. In certain embodiments, the injection temperature is about 65° C.

In some embodiments, the hydrogels of the present disclosure are characterized on the basis of their set up time (i.e., the time required for the hydrogel to provide a stable implant after injection into a patient in need thereof). In some embodiments, the set up time of the hydrogels of the disclosure is characterized by providing an implant that does not come back out from puncture resulting from the injection of the hydrogel. In some embodiments, the set up time of the hydrogels of the present disclosure is less than about 20 minutes, less than about 15 minutes or less than about 10 minutes. In some embodiments, the set up time of the hydrogels of the present disclosure is about 20 minutes, about 15 minutes or about 10 minutes.

In some embodiments, the hydrogels of the present disclosure are described on the basis of the composition of the polymers in the hydrogel. In some embodiments, the present disclosure provides a hydrogel, where the polymer comprises polyvinyl alcohol, polyethylene glycol and an associating polymer. In some embodiments, the present disclosure provides a hydrogel, where the polymer consists essentially of polyvinyl alcohol, polyvinylpyrrolidone and an associating polymer.

In some embodiments, the associating polymer is selected from the group consisting of polyvinylpyrrolidone (PVP), N-(2-hydroxypropyl) methacrylamide (HMPA), xanthan gum, guar gum, pectin, N-carboxymethyl chitosan, polyacrylic acid, hydroxypropyl cellulose (HPC), hydroxypropyl methylcellulose (HPMC), hyaluronic acid, amylose, amylopectin, dextran, and polyacrylamide. In certain embodiments, the associating polymer is polyvinylpyrrolidone.

The hydrogels of the present disclosure may include a suitable solvent. In some embodiments, the suitable solvent is selected from the group consisting of water, saline, phosphate buffer, N-methyl-2-pyrrolidone, dimethylsulfoxide and an aqueous solution of a $C_1$-$C_6$ alcohol (e.g., methanol, ethanol, ethylene glycol). In certain embodiments, the solvent is water.

In some embodiments, the hydrogel contains a contrast agent. The purpose of the contrast agent is to allow the implant to be imaged using standard methods after injection and to confirm the implant was properly placed and that an adequate volume of hydrogel was used in the injection. Suitable contrast agents are known to those skilled in the art. In some embodiments, the contrast agent is selected from the group consisting of an iodine compound, silver, a silver salt and a calcium salt (such as hydroxylapatite). In some embodiments, the contrast agent is barium sulfate. In other embodiments, the contrast agent is silver sulfate.

In some embodiments, the hydrogel comprises
(a) about 12 wt. % to about 22 wt. % of polyvinyl alcohol;
(b) about 0.12 wt. % to about 0.22 wt. % of polyvinylpyrrolidone; and
(c) about 12 wt. % to about 22 wt. % of polyethylene glycol.

In some embodiments, the hydrogel comprises
(a) about 12 wt. % to about 22 wt. % of polyvinyl alcohol;
(b) about 0.12 wt. % to about 0.22 wt. % of polyvinylpyrrolidone;
(c) about 12 wt. % to about 22 wt. % of polyethylene glycol; and
(d) about 9 wt. % to about 19 wt. % of a contrast agent.

In some embodiments, the hydrogel comprises
(a) about 14 wt. % to about 20 wt. % of polyvinyl alcohol;
(b) about 0.14 wt. % to about 0.20 wt. % of polyvinylpyrrolidone; and
(c) about 14 wt. % to about 20 wt. % of polyethylene glycol.

In some embodiments, the hydrogel comprises
(a) about 14 wt. % to about 20 wt. % of polyvinyl alcohol;
(b) about 0.14 wt. % to about 0.20 wt. % of polyvinylpyrrolidone;
(c) about 14 wt. % to about 20 wt. % of polyethylene glycol; and
(d) about 11 wt. % to about 17 wt. % of a contrast agent.

In some embodiments, the hydrogel comprises
(a) about 15 wt. % to about 19 wt. % of polyvinyl alcohol;
(b) about 0.15 wt. % to about 0.19 wt. % of polyvinylpyrrolidone; and
(c) about 15 wt. % to about 19 wt. % of polyethylene glycol.

In some embodiments, the hydrogel comprises
(a) about 15 wt. % to about 19 wt. % of polyvinyl alcohol;
(b) about 0.15 wt. % to about 0.19 wt. % of polyvinylpyrrolidone;
(c) about 15 wt. % to about 19 wt. % of polyethylene glycol; and (d) about 12 wt. % to about 16 wt. % of a contrast agent.

In some embodiments, the hydrogel comprises
(a) about 16 wt. % to about 18 wt. % of polyvinyl alcohol;
(b) about 0.16 wt. % to about 0.18 wt. % of polyvinylpyrrolidone; and
(c) about 16 wt. % to about 18 wt. % of polyethylene glycol.

In some embodiments, the hydrogel comprises
(a) about 16 wt. % to about 18 wt. % of polyvinyl alcohol;
(b) about 0.16 wt. % to about 0.18 wt. % of polyvinylpyrrolidone;
(c) about 16 wt. % to about 18 wt. % of polyethylene glycol; and
(d) about 13 wt. % to about 15 wt. % of a contrast agent.

In some embodiments, the hydrogel comprises
(a) about 17 wt. % of polyvinyl alcohol;
(b) about 0.17 wt. % polyvinylpyrrolidone; and
(c) about 17 wt. % of polyethylene glycol.

In some embodiments, the hydrogel comprises
(a) about 17 wt. % of polyvinyl alcohol;
(b) about 0.17 wt. % polyvinylpyrrolidone;
(c) about 17 wt. % of polyethylene glycol and
(d) about 14 wt. % of a contrast agent.

In a some embodiments, the hydrogel comprises
(a) polyvinyl alcohol;
(b) at least one associating polymer; and
(c) polyethylene glycol
wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa. In certain further embodiments, the associating polymer is polyvinylpyrrolidone.

In a some embodiments, the hydrogel comprises
(a) polyvinyl alcohol;
(b) at least one associating polymer; and
(c) polyethylene glycol
wherein at a temperature of about 65° C. the hydrogel is capable of safe injection into the nucleus of an intervertebral disc of a living patient through a 16 cm length, 17 gauge needle to provide a tissue implant having a mechanical modulus of between about 0.1 to 5.0 MPa. In certain further embodiments, the associating polymer is polyvinylpyrrolidone.

In some embodiments, the hydrogel comprises:
(a) polyvinyl alcohol;
(b) at least one associating polymer;
(c) polyethylene glycol and
(d) a contrast agent,
wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa. In certain further embodiments, the associating polymer is polyvinylpyrrolidone.

In some embodiments, the average molecular weight of the polyethylene glycol is about 100 Da to about 4600 Da, including about 200 Da, about 300 Da, about 400 Da, about 500 Da, about 600 Da, about 700 Da, about 800 Da, about 900 Da, about 1000 Da, about 1100 Da, about 1200 Da, about 1400 Da, about 1600 Da, about 1800 Da, about 2000 Da, about 2200 Da, about 2400 Da, about 2600 Da, about 2800 Da, about 3000 Da, 3200 Da, about 3400 Da, about 3600 Da, about 3800 Da, about 4000 Da, about 4200 Da, and about 4400 Da, and all ranges there in between. In certain embodiments, the average molecular weight of the polyethylene glycol is about 800 Da to about 1200 Da.

In some embodiments, the average molecular weight of the polyethylene glycol is about 100 Da, about 200 Da, about 300 Da, about 400 Da, about 500 Da, about 600 Da, about 700 Da, about 800 Da, about 900 Da, about 1000 Da, about 1100 Da, about 1200 Da, about 1400 Da, about 1600 Da, about 1800 Da, about 2000 Da, about 2200 Da, about 2400 Da, about 2600 Da, about 2800 Da, about 3000 Da, 3200 Da, about 3400 Da, about 3600 Da, about 3800 Da, about 4000 Da, about 4200 Da, about 4400 Da, or about 4600 Da. In certain embodiments, the average molecular weight of the polyethylene glycol is about 1000 Da.

In some embodiments, the average molecular weight of the polyvinyl alcohol is about 60,000 Da to about 190,000 Da, including about 65,000 Da, about 70,000 Da, about 75,000 Da, about 80,000 Da, about 85,000 Da, about 90,000 Da, about 95,000 Da, about 100,000 Da, about 105,000 Da, about 110,000 Da, about 115,000 Da, about 120,000 Da, about 125,000 Da, about 130,000 Da, about 135,000 Da, about 140,000 Da, about 145,000 Da, about 150,000 Da, about 155,000 Da, about 160,000 Da, about 165,000 Da, 165,000 Da, about 170,000 Da, about 175,000 Da, about 180,000 Da, and about 185,000 Da, and all ranges there in between. In certain embodiments, the average molecular weight of the polyvinyl alcohol is about 135,000 Da to about 155,000 Da.

In some embodiments, the average molecular weight of the polyvinyl alcohol is about 60,000 Da, about 65,000 Da, about 70,000 Da, about 75,000 Da, about 80,000 Da, about 85,000 Da, about 90,000 Da, about 95,000 Da, about 100,000 Da, about 105,000 Da, about 110,000 Da, about 115,000 Da, about 120,000 Da, about 125,000 Da, about 130,000 Da, about 135,000 Da, about 140,000 Da, about 145,000 Da, about 150,000 Da, about 155,000 Da, about 160,000 Da, about 165,000 Da, 165,000 Da, about 170,000 Da, about 175,000 Da, about 180,000 Da, about 185,000 Da or about 190,000 Da. In certain embodiments, the average molecular weight of the polyvinyl alcohol is about 145,000 Da.

In some embodiments, the average molecular weight of the polyvinylpyrrolidone is about 5,000 Da to about 60,000 Da, including about 10,000 Da, about 15,000 Da, about 20,000 Da, about 25,000 Da, about 30,000 Da, about 35,000 Da, about 40,000 Da, about 45,000 Da, about 50,000 Da, and about 55,000 Da, and all ranges there in between. In certain embodiments, average molecular weight of the polyvinylpyrrolidone is about 35,000 Da to about 45,000 Da.

In some embodiments, the average molecular weight of the polyvinylpyrrolidone is about 5,000 Da, about 10,000 Da, about 15,000 Da, about 20,000 Da, about 20,000 Da, about 25,000 Da, about 30,000 Da, about 35,000 Da, about 40,000 Da, about 45,000 Da, about 50,000 Da, about 55,000 Da, or about 60,000 Da. In certain embodiments, average molecular weight of the polyvinylpyrrolidone is about 40,000 Da.

In some embodiments, the K-value of the polyvinylpyrrolidone is about 26 to about 34, including about 27, about 28, about 29, about 30, about 31, about 32 and about 33, and all ranges there in between. In certain embodiments, the K-value of the polyvinylpyrrolidone is about 28 to about 32. The K-values described herein are determined using capillary viscometry according to the method set forth in ISO 1628-1.

In some embodiments, the K-value of the polyvinylpyrrolidone is about 26, about 27, about 28, about 29, about 30, about 31, about 32, about 33 or about 34. In certain embodiments, the K-value of the polyvinylpyrrolidone is about 30.

In one aspect, the present disclosure provides kits containing the compositions of the present disclosure packaged in a suitable container. The volume of the compositions of the present disclosure in the suitable container will depend on the particular application.

In some embodiments, the present disclosure provides a kit for disc augmentation (i.e., repair of a damaged disc). In some embodiments, the present disclosure provides a kit for disc augmentation comprising about 0.5 cc to about 2.0 cc, including about 1.0 cc, about 1.5 cc, and all ranges there between, of a composition of the present disclosure packaged in a suitable container. In some embodiments, the present disclosure provides a kit for disc augmentation comprising about 0.5 cc, about 1.0 cc, about 1.5 cc, or about 2.0 cc of a composition of the present disclosure packaged in a suitable container In some embodiments, the present disclosure provides a kit for nucleus pulposus replacement (i.e., to replace a nucleus pulposus that has been enucleated). In some embodiments, the present disclosure provides a kit for nucleus pulposus replacement comprising about 1.0 cc to about 4.0 cc, including about 1.5 cc, about 2.0 cc, about 2.5 cc, about 3.0 cc and about 3.5 cc, and all ranges there between, of a composition of the present disclosure packaged in a suitable container. In some embodiments, the present disclosure provides a kit for nucleus pulposus replacement comprising about 1.0 cc, about 1.5 cc, about 2.0 cc, about 3.0 cc, about 3.5 cc, or about 4.0 cc of a composition of the present disclosure packaged in a suitable container.

Suitable containers for packaging the hydrogels of the present disclosure are known to those skilled in the art. In some embodiments, the suitable container is selected from a vial or a syringe. In some embodiments, the suitable container is glass. In other embodiments, the suitable container is polycarbonate. In certain embodiments, the suitable container is a polycarbonate syringe. In certain embodiments, the suitable container is a glass syringe.

In some embodiments, the kits of the present disclosure further comprise a hydrogel delivery system. Suitable hydrogel delivery systems are capable of receiving a hydrogel of the present disclosure, maintaining the temperature of the hydrogel within a desired range prior to and during injection, and injecting a hydrogel of the present disclosure through a fine gauge needle into the tissue of a patient in need thereof (for example, the nucleus of an intervertebral disc) under temperature and pressure conditions that are safe for injection into a living patient.

In certain embodiments, the hydrogel delivery system comprises a gun and a syringe assembly. In certain embodiments, the gun and syringe assembly is the assembly shown in FIG. 1. Referring to FIG. 1, some embodiments provide a gun and syringe assembly 100 ("Assembly 100") for use in the kits and methods of the present disclosure. In some embodiments, Assembly 100 is provided in a kit that may be used to repair or supplement the nucleus pulposus of a patient in need thereof.

FIG. 1 shows an injection gun 110 that is coupled to a syringe 130 for injection of a hydrogel of the present disclosure into a nucleus pulposus 52 of a vertebral disc 50.

In some embodiments, prior to injection, a hydrogel of the present disclosure is heated to about 121° C. in an autoclave and inserted into syringe 130. In some embodiments, syringe 130 is pre-packed with a hydrogel of the present disclosure and the hydrogel-containing syringe 130 is heated. A heating coil is optionally wrapped around the exterior of syringe 130 to maintain temperature of the hydrogel in the syringe barrel 130.

A flexible extension tubing 150 is connected to the discharge end of the syringe 130. In some embodiments, the tubing 150 is constructed from a medical grade polymer, such as polyurethane, and is about 160 mm long and have an inner diameter of about 1.59 mm. In some embodiments, the flexible extension tubing 150 is about 10 inches long. In some embodiments, the flexible extension tubing 150 is about 6 inches long. However, those skilled in the art will recognize that the tubing 150 can be other lengths and inner diameters. The flexibility of the flexible extension tubing 150 provides the surgeon with a degree of freedom and allows the surgeon to move around during the hydrogel injection process, enabling the surgeon to monitor the injection process through a real-time computed tomography (CT) scan.

The needle 170 has a discharge end 172 that is inserted through the wall of the disc 50 into the nucleus pulposus 52 for injection of the hydrogel. In one embodiment, the needle 170 is a 20 gauge needle. In other embodiments, the gauge of the needle 170 is selected from the group consisting of about 15 gauge, about 16 gauge, about 17 gauge, about 18 gauge, about 19 gauge, about 20 gauge, about 21 gauge, and about 22 gauge. In other embodiments, the gauge of the needle 170 is greater than about 17 gauge, such as about 15 gauge or about 16 gauge. Fine gauge needle minimize the size of the injection opening through the wall of the disc 50, thereby minimizing the size of the opening through which the hydrogel can escape from the disc 50 after the needle 170 is removed from the disc 50 following injection.

Method of Making Hydrogel:

In one aspect, the present disclosure provides methods of making the hydrogels of the present disclosure.

In some embodiments, the method of manufacturing a hydrogel comprises:
(a) forming a mixture of at least one polymer and a solvent;
(b) stirring the mixture of step (a);
(c) melting the stirred mixture of step (b) to form a solution; and
(d) cooling the solution of step (c) to provide a hydrogel, wherein at a temperature of about 65° C. the hydrogel is capable of injection through a 16 cm length, 17 gauge needle at an injection rate of at least 2.0 cc per minute using an injection pressure of about 50 p.s.i. to provide a tissue implant having a mechanical modulus of between about 0.1 to 5.0 MPa.

In some embodiments, the method of manufacturing a hydrogel comprises:
(a) forming a mixture of at least one polymer and a solvent;
(b) stirring the mixture of step (a);
(c) melting the stirred mixture of step (b) to form a solution; and
(d) cooling the solution of step (c) to provide a hydrogel, wherein at a temperature of about 65° C. the hydrogel is capable of safe injection into the nucleus of an intervertebral disc of a living patient through a 16 cm length, 17 gauge needle to provide a tissue implant having a mechanical modulus of between about 0.1 to 5.0 MPa.

In some embodiments, at least one polymer is a mixture of polyvinyl alcohol, polyvinylpyrrolidone, polyethylene glycol and the solvent is water. In some embodiments, the mixture of step (a) further comprises a contrast agent. In some embodiments, the contrast agent is barium sulfate. In some embodiments, the contrast agent is silver sulfate.

In some embodiments, the mixture of step (a) consists essentially of:
(1) about 7 wt. % to about 17 wt. % of polyvinyl alcohol;
(2) about 0.07 wt. % to about 0.17% of polyvinylpyrrolidone;
(3) about 13 wt. % to about 23 wt. % of polyethylene glycol;
(4) about 3 wt. % to about 13 wt. % of a contrast agent and
(5) about 57 wt. % to about 67 wt. % of water.

In some embodiments, the mixture of step (a) consists essentially of:
(1) about 9 wt. % to about 15 wt. % of polyvinyl alcohol;
(2) about 0.09 wt. % to about 0.15% of polyvinylpyrrolidone;
(3) about 15 wt. % to about 21 wt. % of polyethylene glycol;
(4) about 5 wt. % to about 11 wt. % of a contrast agent and
(5) about 59 wt. % to about 65 wt. % of water.

In some embodiments, the mixture of step (a) consists essentially of:
(1) about 11 wt. % to about 13 wt. % of polyvinyl alcohol;
(2) about 0.11 wt. % to about 0.13% of polyvinylpyrrolidone;
(3) about 17 wt. % to about 19 wt. % of polyethylene glycol;
(4) about 7 wt. % to about 9 wt. % of a contrast agent and
(5) about 61 wt. % to about 63 wt. % of water.

In some embodiments, the present disclosure provides a method of manufacturing a hydrogel comprising:
(1) about 12 wt. % to about 22 wt. % of polyvinyl alcohol;
(2) about 0.12 wt. % to about 0.22 wt. % of polyvinylpyrrolidone;
(3) about 12 wt. % and about 22 wt. % polyethylene glycol; and
(4) a solvent,
the method comprising:
(a) forming a mixture of polyvinyl alcohol, polyvinylpyrrolidone, polyethylene glycol and a solvent;
(b) stirring the mixture of step (a);
(c) melting the stirred mixture of step (b) to form a solution; and
(d) cooling the solution of step (c).

In some embodiments, the present disclosure provides hydrogels prepared according to the methods described herein.

Implants:

In one aspect, the present invention provides a tissue implant having a mechanical modulus of between about 0.1 to 5.0 MPa, wherein the tissue implant is formed by the injection of a hydrogel the present disclosure into a living patient's tissue. The tissue implants of the present disclosure are suitable to repair and supplement a variety of tissues, including repair of damage articular cartilage, bulking agent to support the urethra (for the treatment of incontinence or vesicoureteral reflux); repair or replacement of the nucleus pulposus of an intervertebral disc and a filler for use in cosmetic applications. In some embodiments, the tissue implants of the present disclosure are suitable to repair and replace the nucleus pulposus of an intervertebral disc.

In some embodiments, the tissue implants of the present disclosure have a mechanical modulus of between about 0.1 to 5.0 MPa, and the tissue implant is formed by the injection of a hydrogel into a living patient's tissue, wherein the hydrogel comprises:
at least one polymer; and
a solvent,
wherein at a temperature of about 65° C. the hydrogel is capable of injection through a 16 cm length, 17 gauge needle at an injection rate of at least 2.0 cc per minute using an injection pressure of about 50 p.s.i.

In some embodiments, the tissue implants of the present disclosure have a mechanical modulus of between about 0.1 to 5.0 MPa, and the tissue implant is formed by the injection of a hydrogel into the nucleus of an intervertebral disc of a living patient, wherein the hydrogel comprises:
at least one polymer; and
a solvent,
wherein at a temperature of about 65° C. the hydrogel is capable of safe injection into the nucleus of an intervertebral disc of a living patient.

In some embodiments, the tissue implants of the present disclosure have a mechanical modulus of between about 0.1 to 5.0 MPa, and the tissue implant is formed by the injection of a hydrogel into the nucleus of an intervertebral disc of a living patient, wherein the hydrogel comprises:
at least one polymer; and
a solvent,
wherein at a temperature of about 65° C. the hydrogel is capable of safe injection into the nucleus of an intervertebral disc of a living patient through a 16 cm length, 17 gauge needle at an injection rate of at least 1.0 cc per minute, wherein the backpressure during the injection is from about 60 p.s.i. to about 200 p.s.i.

In some embodiments, the tissue implants of the present disclosure have a mechanical modulus of between about 0.1 to 5.0 MPa, and the tissue implant is formed by the injection of a hydrogel into a living patient's tissue, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent.

In some embodiments, the tissue implants of the present disclosure have a mechanical modulus of between about 0.1 to 5.0 MPa, and the tissue implant is formed by the injection of a hydrogel into a living patient's tissue, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent,
wherein at a temperature of about 65° C. the hydrogel is capable of injection through a 16 cm length, 17 gauge needle at an injection rate of at least 2.0 cc per minute using an injection pressure of about 50 p.s.i.

In some embodiments, the tissue implants of the present disclosure have a mechanical modulus of between about 0.1 to 5.0 MPa, and the tissue implant is formed by the injection of a hydrogel into the nucleus of an intervertebral disc of a living patient, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and a solvent,
wherein at a temperature of about 65° C. the hydrogel is capable of safe injection into the nucleus of an intervertebral disc of a living patient.

In some embodiments, the tissue implants of the present disclosure have a mechanical modulus of between about 0.1 to 5.0 MPa, and the tissue implant is formed by the injection of a hydrogel into the nucleus of an intervertebral disc of a living patient, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent,
wherein at a temperature of about 65° C. the hydrogel is capable of safe injection into the nucleus of an intervertebral disc of a living patient through a 16 cm length, 17 gauge needle at an injection rate of at least 1.0 cc per minute, wherein the backpressure during the injection is from about 60 p.s.i. to about 200 p.s.i.

In some embodiments, the mechanical modulus of the implant is about 0.1 MPa to about 5 MPa, including about 0.5 MPa, about 1.0 MPa, about 1.5 MPa, about 2.0 MPa, about 2.5 MPa, about 3.0 MPa, about 3.5 MPa, about 4.0 MPa, and about 4.5 MPa, and all ranges there in between. In certain embodiments, the mechanical modulus of the implant is about 1.0 MPa to about 2.0 MPa. In certain embodiments, the mechanical modulus of the implant is about 0.1 MPa to about 1.0 MPa.

In some embodiments, the mechanical modulus of the implant is about 0.1 MPa, about 0.5 MPa, about 1.0 MPa, about 1.5 MPa, about 2.0 MPa, about 2.5 MPa, about 3.0 MPa, about 3.5 MPa, about 4.0 MPa, about 4.5 MPa or about 5.0 MPa. In certain embodiments, mechanical modulus of the implant is about 0.1 MPa. In certain embodiments, mechanical modulus of the implant is about 0.5 MPa.

Methods of Use:

In one aspect, the present disclosure provides methods of repairing or supplementing a tissue by administering a therapeutically effective amount of a hydrogel of the present disclosure to a patient in need thereof to provide a tissue implant. The methods of the present disclosure are suitable to repair and supplement a variety of tissues, including to repair damaged articular cartilage, bulking to support the urethra (for the treatment of incontinence or vesicoureteral reflux), repairing or replacing the nucleus pulposus of an intervertebral disc and filling for cosmetic applications.

The hydrogels of the present disclosure may be injected into the patient tissue using any suitable hydrogel delivery device. In some embodiments, the hydrogels of the present disclosure are injected using hydrogel delivery devices described in U.S. Pat. No. 8,475,532, which is hereby incorporated by reference in its entirety. In some embodiments, the hydrogels of the present disclosure are injected using the hydrogel delivery device described in FIG. 1.

In some embodiments, the method of repairing or supplementing a tissue in a patient in need thereof, comprises:
(a) filling a syringe with a hydrogel of the present disclosure;
(b) heating the hydrogel of step (a) to from about 60° C. to about 75° C.;
(c) connecting a 15 gauge or smaller needle to the syringe;
(d) inserting the needle into the tissue in need of repair or supplement; and
(e) injecting a therapeutically effective amount of the hydrogel into the tissue to provide a tissue implant having a mechanical modulus of between about 0.1 to 5.0 MPa.

The therapeutically effective amount of the hydrogel injected in the methods of the present disclosure depends on the tissue that is repaired or supplemented and may be determined by those of skill in the art.

In some embodiments, the present disclosure provides methods of repairing or supplementing the nucleus of an intervertebral disc in a patient in need thereof. In some embodiments, the method of repairing or supplementing the nucleus of an intervertebral disc in a patient in need thereof, comprises:
(a) filling a syringe with a hydrogel comprising at least one polymer and a solvent;
(b) heating the hydrogel of step (a) to about 65° C.;
(c) connecting a 15 gauge or smaller needle to the syringe;
(d) inserting the needle into the nucleus of an intervertebral disc in need of repair or supplement; and
(e) injecting a therapeutically effective amount of the hydrogel into the nucleus of an intervertebral disc to provide a tissue implant, wherein at a temperature of about 65° C. the hydrogel is capable of safe injection into the nucleus of an intervertebral disc of a living patient through a 16 cm length, 17 gauge needle at an injection rate of at least 1.0 cc per minute provide a tissue implant having a mechanical modulus of between about 0.1 to 5.0 MPa, wherein the backpressure during the injection is from about 35 p.s.i. to about 400 p.s.i.

In some embodiments, the backpressure during the injection of a therapeutically effective amount of the hydrogel into the nucleus of an intervertebral disc to provide a tissue implant having a mechanical modulus of between about 0.1 to 5.0 MPa is from about 35 p.s.i. to about 400 p.s.i., including about 40 p.s.i., about 50 p.s.i., about 60 p.s.i., about 70 p.s.i., about 80 p.s.i., about 90 p.s.i., about 100 p.s.i., about 110 p.s.i., about 120 p.s.i., about 130 p.s.i., about 140 p.s.i., about 150 p.s.i., about 160 p.s.i., about 170 p.s.i., about 180 p.s.i., about 190 p.s.i., about 200 p.s.i., about 210 p.s.i., about 220 p.s.i., about 230 p.s.i., about 240 p.s.i., about 250 p.s.i., about 260 p.s.i., about 270 p.s.i., about 280 p.s.i., about 290 p.s.i., about 300 p.s.i., about 310 p.s.i., about 320 p.s.i., about 330 p.s.i., about 340 p.s.i., about 350 p.s.i., about 360 p.s.i., about 370 p.s.i., about 380 p.s.i., and about 390 p.s.i., and all ranges there in between. In certain embodiments, the backpressure during the injection of a therapeutically effective amount of the hydrogel into the nucleus of an intervertebral disc to provide a tissue implant having a mechanical modulus of between about 0.1 to 5.0 MPa is from about 60 p.s.i. to about 200 p.s.i.

In some embodiments, the method of repairing or supplementing the nucleus of an intervertebral disc in a patient in need thereof, comprises:
(a) filling a syringe with a hydrogel comprising at least one polymer and a solvent;
(b) heating the hydrogel of step (a) to about 65° C.;
(c) connecting a 15 gauge or smaller needle to the syringe;
(d) inserting the needle into the nucleus of an intervertebral disc in need of repair or supplement; and
(e) injecting a therapeutically effective amount of the hydrogel into the nucleus of an intervertebral disc to provide a tissue implant, wherein at a temperature of about 65° C. the hydrogel is capable of safe injection into the nucleus of an intervertebral disc of a living patient through a 16 cm length, 17 gauge needle at an injection rate of at least 1.0 cc per minute provide a tissue implant having a mechanical modulus of between about 0.1 to 5.0 MPa, wherein the maximum backpressure during the injection is about 400 p.s.i.

In some embodiments, the maximum backpressure during the injection of a therapeutically effective amount of the hydrogel into the nucleus of an intervertebral disc to provide a tissue implant having a mechanical modulus of between about 0.1 to 5.0 MPa is less than about 60 p.s.i., about 70 p.s.i., about 80 p.s.i., about 90 p.s.i., about 100 p.s.i., about 110 p.s.i., about 120 p.s.i., about 130 p.s.i., about 140 p.s.i., about 150 p.s.i., about 160 p.s.i., about 170 p.s.i., about 180 p.s.i., about 190 p.s.i., about 200 p.s.i., about 210 p.s.i., about 220 p.s.i., about 230 p.s.i., about 240 p.s.i., about 250 p.s.i., about 260 p.s.i., about 270 p.s.i., about 280 p.s.i., about 290 p.s.i., about 300 p.s.i., about 310 p.s.i., about 320 p.s.i., about 330 p.s.i., about 340 p.s.i., about 350 p.s.i., about 360 p.s.i., about 370 p.s.i., about 380 p.s.i., about 390 p.s.i., and about 400 p.s.i. In certain embodiments, the maximum backpressure during the injection of a therapeutically effective amount of the hydrogel into the nucleus of an intervertebral disc to provide a tissue implant having a mechanical modulus of between about 0.1 to 5.0 MP is less than about 250 p.s.i. In certain embodiments, the maximum backpressure during the injection of a therapeutically effective amount of the hydrogel into the nucleus of an intervertebral disc to provide a tissue implant having a mechanical modulus of between about 0.1 to 5.0 MP is less than about 200 p.s.i.

Figure 2:
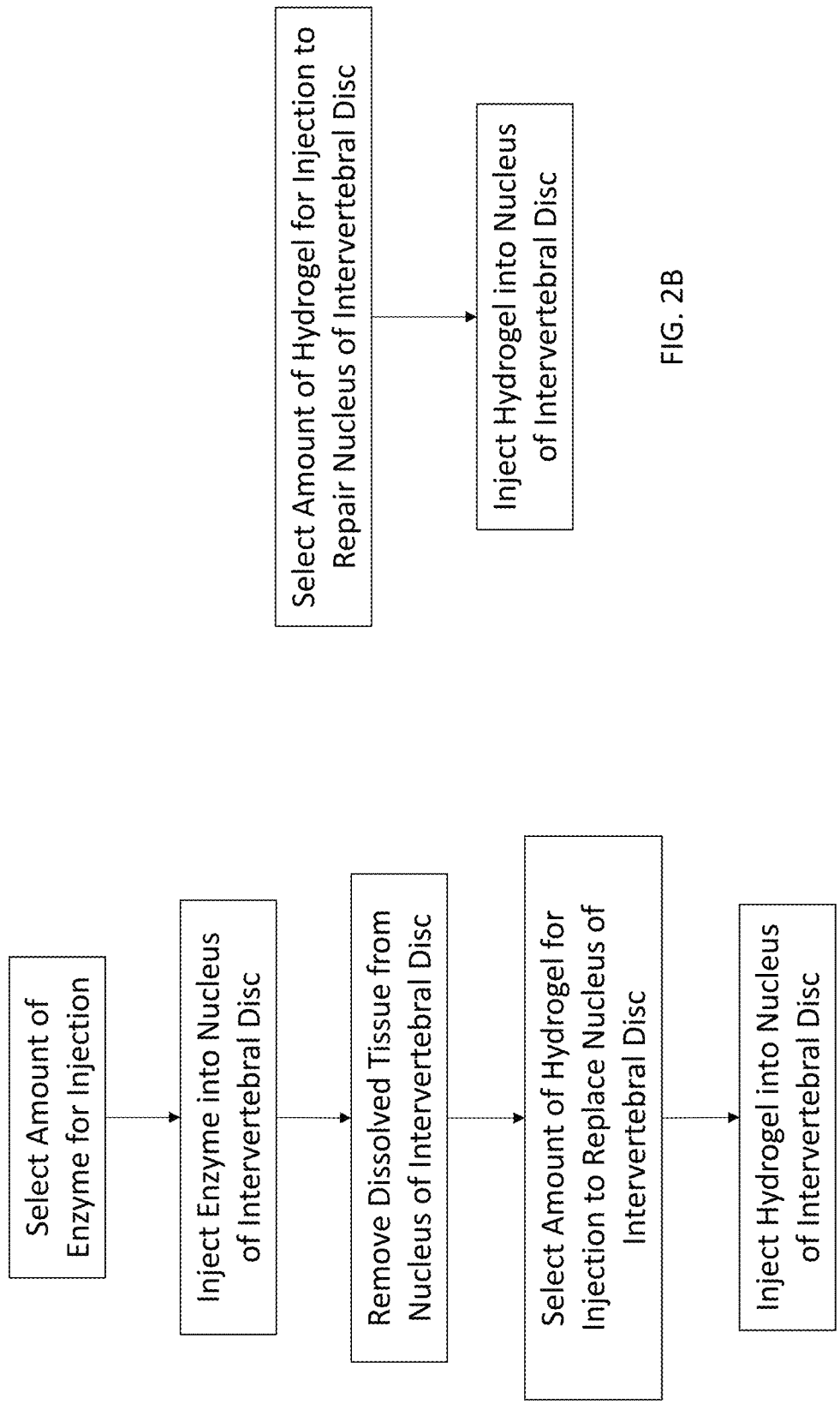
FIG. 2A shows a method of the present disclosure for replacing the nucleus of an intervertebral disc.
FIG. 2B shows a method of the present disclosure for repairing the nucleus of an intervertebral disc.

In some embodiments, the present disclosure provides a method for repairing a nucleus pulposus in a patient in need thereof (e.g., as shown in FIG. 2B). In some embodiments, the method for repairing a degenerated disc in a patient in need thereof comprises injecting about 0.1 to about 2.5 cc, including about 0.1 cc, about 0.5 cc, about 1.0 cc, about 1.5 cc, about 2.0 cc and about 2.5 cc, and all ranges there in between. In certain embodiments, the method for repairing a degenerated disc in a patient in need thereof comprises injecting from 0.5 to about 2.0 cc.

In some embodiments, the hydrogel of step (a) is heated to about 120° C. to reduce the viscosity of the hydrogel and the temperature is reduced to from about 60° C. to about 75° C. in step (b) to allow safe injection of the hydrogel into the patient. In certain embodiments, the hydrogel of step (a) is heated to about 120° C. to reduce the viscosity of the hydrogel and the temperature is reduced to about 65° C. in step (b) to allow safe injection of the hydrogel into the patient.

In some embodiments, the present disclosure provides a method for replacing a nucleus pulposus in a patient in need thereof. In these embodiments, the nucleus pulposus is removed (or enucleated) to provide a cavity into which the compositions of the present disclosure are injected. The nucleus pulposus may be removed using methods that are known to those skilled in the art including the methods described in U.S. Pat. No. 8,475,532 and U.S. Patent Publication No. 2008/0027554, which are hereby incorporated by reference in their entirety for all purposes. In some embodiments, the method for replacing a nucleus pulposus in a patient in need thereof comprises (a) injecting an enzyme into the nucleus of intervertebral disc to dissolve the nucleus pulposus in need of replacement, (b) removing the dissolved tissue from nucleus of the intervertebral disc, and (c) injecting a therapeutically effective amount of a hydrogel of the present disclosure into the nucleus of intervertebral disc as described in FIG. 2A. A person of ordinary skill in the art (for example, a surgeon) could select an appropriate amount of an enzyme used in Step (a) as well as the amount of hydrogel used in Step (c). In some embodiments, the enzyme is a serine protease. In some embodiments, the enzyme is a Chondroitinase enzyme.

In some embodiments, the methods of the present disclosure provide a tissue implant having a mechanical modulus of about 0.1 MPa to about 5 MPa, including about 0.5 MPa, about 1.0 MPa, about 1.5 MPa, about 2.0 MPa, about 2.5 MPa, about 3.0 MPa, about 3.5 MPa, about 4.0 MPa, and about 4.5 MPa, and all ranges there in between. In certain embodiments, the methods of the present disclosure provide a tissue implant having a mechanical modulus of about 1.0 MPa to about 2.0 MPa. In certain embodiments, the methods of the present disclosure provide a tissue implant having a mechanical modulus of about 0.1 MPa to about 1.0 MPa.

In some embodiments, the methods of the present disclosure provide a tissue implant having a mechanical modulus of about 0.1 MPa, about 0.5 MPa, about 1.0 MPa, about 1.5 MPa, about 2.0 MPa, about 2.5 MPa, about 3.0 MPa, about 3.5 MPa, about 4.0 MPa, about 4.5 MPa or about 5.0 MPa. In certain embodiments, the methods of the present disclosure provide a tissue implant having a mechanical modulus of about 0.1 MPa. In certain embodiments, the methods of the present disclosure provide a tissue implant having a mechanical modulus of about 0.5 MPa.

In some embodiments, the needle in Step (c) has a needle gauge of about 15 gauge to about 22 gauge, including about 16 gauge, about 17 gauge, about 18 gauge, about 19 gauge, about 20 gauge, and about 21 gauge, and all ranges there in between. In certain embodiments, the needle gauge is about 17 gauge to about 19 gauge. In some embodiments, the needle in Step (c) has a needle gauge of about 15 gauge, about 16 gauge, about 17 gauge, about 18 gauge, about 19 gauge, about 20 gauge, about 21 gauge, or about 22 gauge. In certain embodiments, the needle in Step (c) has a needle gauge of about 17 gauge. In certain embodiments, the needle in Step (c) is a 152 mm Tuohy epidural needle.

In some embodiments, in Step (c), the needle is connected to the syringe via a flexible extension tube. In some embodiments, the flexible extension tube is constructed from a medical grade polymer, such as polyurethane. In some embodiments, the flexible extension tube is about 10 inches long. In some embodiments, the flexible extension tube is about 6 inches long. In certain embodiments, the flexible extension tube is about 160 mm long and has an inner diameter of about 1.59 mm.

In some embodiments, the injection rate of the hydrogel in Step (e) is greater than about 1.0 cc/min. In some embodiments, the injection rate of the hydrogel in Step (e) is greater than about 1.5 cc/min. In some embodiments, the injection rate of the hydrogel in Step (e) is greater than about 2.0 cc/min. In some embodiments, the injection rate of the hydrogel in Step (e) is greater than about 2.5 cc/min. In some embodiments, the injection rate of the hydrogel in Step (e) is greater than about 3.0 cc/min. In some embodiments, the injection rate of the hydrogel in Step (e) is greater than about 3.5 cc/min. In some embodiments, the injection rate of the hydrogel in Step (e) is greater than about 4.0 cc/min. In some embodiments, the injection rate of the hydrogel in Step (e) is greater than about 4.5 cc/min. In some embodiments, the injection rate of the hydrogel in Step (e) is greater than about 5.0 cc/min. In some embodiments, the injection rate of the hydrogel in Step (e) is greater than about 5.5 cc/min. In some embodiments, the injection rate of the hydrogel in Step (e) is greater than about 6.0 cc/min.

EXAMPLES

The present invention is further illustrated by reference to the following Examples. However, it is noted that these Examples, like the embodiments described above, are illustrative and are not to be construed as restricting the scope of the invention in any way.

Example 1: Preparation of Hydrogels of the Present Disclosure

Exemplary hydrogels of the present disclosure were prepared according to the following procedure. Raw materials were provided in the ratios shown in Table 1, below.

TABLE 1

| Raw Material Composition | | | |
|---|---|---|---|
| Material | Ex. 1A (wt. %) | Ex. 1B (wt. %) | Ex. 1C (wt. %) |
| Polyvinyl Alcohol (MW ~ 145,000 Da) | 12.4% | 12.4% | 22.3% |
| Polyvinylpyrrolidone (MW ~ 45,000 kDa) | 0.124% | 0.124% | 0.223% |
| Polyethylene Glycol (MW ~ 1,000 kDa) | 17.50% | 17.50% | 22.5% |
| Barium Sulfate | 8.3% | — | 6.5% |
| Silver Sulfate | — | 8.3% | — |
| Water | 61.70% | 61.70% | 48.5% |

The following raw materials were used: Polyvinyl alcohol (Polyvinyl alcohol 28-99 available from EMD Millipore), Polyvinylpyrrolidone (Povidone K-30 available from Spectrum Chemical), Polyethylene Glycol (Polyethylene Glycol 1000, NF available from Spectrum Chemical), Barium Sulfate (Barium Sulfate, U.S.P. available from J.T. Baker).

The PVA, PVP and contrast agent solutions were prepared by mixing the PVA, PVP and contrast agent in water using the masses recited in Table 2. The PVA, PVP and contrast agent solutions were stirred for about two minutes. The resulting mixtures were heated to above the melting point (but not more than 200 degrees Celsius), and the solutions were held at this temperature for about 30 minutes. The temperature of the solutions was adjusted to about 85° C. and PEG was added to the solutions.

TABLE 2

| Raw Material Mass | | | | | | | |
|---|---|---|---|---|---|---|---|
| | PVA, PVP and Contrast agent solution | | | | | | PEG |
| Example | PVA (g) | PVP (g) | BaSO$_4$ (g) | AgSO$_4$ (g) | water (g) | Total Mass (g) | PEG (g) |
| Ex. 1A | 13.98 | 0.14 | 9.34 | — | 69.77 | 93.23 | 19.77 |
| Ex. 1B | 13.98 | 0.14 | — | 9.34 | 69.77 | 93.23 | 19.77 |
| Ex. 1C | 25.20 | 0.25 | 7.35 | — | 54.81 | 87.60 | 24.42 |

The solutions were placed in a sealed container at about 22° C. for about three hours. After about three hours, the containers were opened and the supernatants decanted and their weights recorded. The recorded weights were used to establish mass balance throughout the manufacturing process to the finished hydrogel. The polymer solutions were resealed in their respective containers and heated for about 30 minutes at 121° C.

Within 10 minutes after the end of the heating cycle, the containers were removed from the heat and supernatants were decanted, its weight is recorded, and discarded. The contents of the container were stirred for three minutes. The finished hydrogels were packaged in syringes.

Example 2: Injection of the Hydrogels of the Present Disclosure

The following example provides a representative injection procedure for replacing a nucleus pulposus as well as certain injection properties of the hydrogels of the present disclosure.

Example 2a: Injection Procedure

Prior to use, the hydrogel-containing syringes prepared according to Example 1 may be heated for about 30 minutes at 121° C., and cooled to about 65° C. to reduce the hydrogel viscosity to about 10.7+/−1.3 Pascal seconds (Pa·s) prior to injection.

Referring to FIG. 1, the hydrogel may injected into an intervertebral disc 50 using the injection apparatus described above and in FIG. 1. The injection apparatus 110 is connected to a length of flexible, high-pressure tubing 150 that is in turn connected to an injection needle 170. The arrangement allows the surgeon freedom of movement between the injection apparatus 110 and the needle 170.

The tubing 150 may be about 25 cm in length. With a syringe temperature of about 65° C., it is estimated that the hydrogel cools to about 50° C. due cooling during passage through the tubing 150 (25 cm in length) to the needle 170. This is a temperature high enough to allow flow (viscosity of about 25.1+/−6.4 Pa·s) but does not burn patient's tissue.

Prior to injecting the hydrogel into the disc, the disc can be de-nucleated by any of several known methods through the needle 170. For a nucleus having a volume of 1.8 cc, the volume can be filled with a hydrogel of the present disclosure in 46 seconds using an 18 gauge needle and in 42 seconds using a 17 gauge needle.

Example 2b: Injection Properties

Experiments were conducted to determine the injection properties of the hydrogels of the present disclosure.

The hydrogels Examples 1A and 1D were placed in 3 mL syringes and injected through either a 17 gauge or 20 gauge 15.2 cm Tuohy epidural Needle connected to the syringe by a high pressure tube (length: 10-inch (or 25.4 cm); inner diameter: 0.071 inch (or 1.8034 mm)) while heated using a syringe heater at 65° C. Thus, the total path length between the heated syringe and the needle tip was about 40.6 cm.

Table 3 shows the pressure and force required to inject the Example 1A hydrogel through the 17 gauge needle. These data show that the Example 1A hydrogel may be injected at rates of 5.9 mL/min through a 17 gauge needle with a path length of 40.6 cm between the heated syringe and the needle.

TABLE 3

| Injection Pressure and Force | | | | | | |
|---|---|---|---|---|---|---|
| Rate | Raw Force (N) | | Pressure (kPa) | | Pressure (psi) | |
| (ml/min) | Avg. | St. Dev | Avg. | St. Dev | Avg. | St. Dev |
| 1 | 10.2 | 8.1 | 170 | 134 | 24.6 | 19.5 |
| 2 | 21.1 | 2.5 | 349 | 41 | 50.6 | 6.0 |
| 4 | 22.3 | 2.8 | 369 | 47 | 53.4 | 6.8 |
| 5.9 | 54.5 | 34.7 | 902 | 574 | 130.8 | 83.2 |

The test syringes failed when attempts were made to inject the hydrogel of Example 1A at through a 20 gauge needle and when the hydrogel of Example 1D was attempted through a 17 gauge or 20 gauge needle.

Example 3: Compositional Change: Raw Materials→Hydrogels→Implants of the Present Disclosure The hydrogels and implants of the present disclosure do not require chemical crosslinking agents for gelation. Instead, the present hydrogels result from physical crosslinking due to interchain hydrogen bonding between the constituent polymers (e.g., PVA, PVP and PEG) and intrachain hydrogen bonding due to polymer crystallization.

Persons of ordinary skill in the art will understand that because the present hydrogels are based on hydrogen bonding rather than chemical crosslinking (which is found in many other hydrogels), the composition of the input raw materials and the resulting hydrogels are not the same. Specifically, during manufacturing the raw materials are combined to provide the hydrogel and the aqueous supernatants from above the hydrogels are decanted (see, e.g., Example 1). The aqueous supernatants contain free polymers (i.e., not equilibrated into the hydrogel) in ratios that are not identical to the ratios found in the raw materials. Similarly, following injection, the composition of the implants of the present disclosure is different from the injected hydrogel compositions.

Table 4 shows the change in composition of Example 1A, from the input raw materials, the packaged hydrogel in the syringe and the concentrations by weight after allowing the composition to swell in a simulated spine disc environment (i.e., 0.2 MPa osmotic solution at 37 degrees Celsius) for one week:

TABLE 4

Compositional change for Example 1A

| Material | Raw Materials | Gel in Syringe | Gel in simulated spine disc for 7 days |
|---|---|---|---|
| Polyvinyl Alcohol (MW ~ 145,000 Da) | 12.4% | 17.0% | 13.9% |
| Polyvinylpyrrolidone (MW ~ 45,000 kDa) | 0.124% | 0.170% | 0.140% |
| Polyethylene Glycol (MW ~ 1,000 kDa) | 17.50% | 13.8% | 13.8% |
| Barium Sulfate | 8.3% | 16.8% | 6.2% |
| Water | 61.70% | 52.5% | 64.1% |

Example 4: In Vivo Model Using the Hydrogels of the Present Disclosure

The following example will establish proof of concept regarding the use of the hydrogels of the present disclosure to treat degenerative disc disease in a large mammal. The purpose of the study is to demonstrate test article delivery (i.e., delivery of the hydrogels of the present disclosure), postoperative survival and in vivo performance of the hydrogels of the present disclosure using in situ chemonucleolysis followed by nucleoplasty in a goat model that recapitulates intervertebral disc degeneration. Chemonucleolysis will be conducted using Chondroitinase ABC protease free (lyophilized) ("CABC").

Test Article:

A hydrogel having the composition of Example 1a (Tables 1-3, above) will be supplied.

Figure 3:
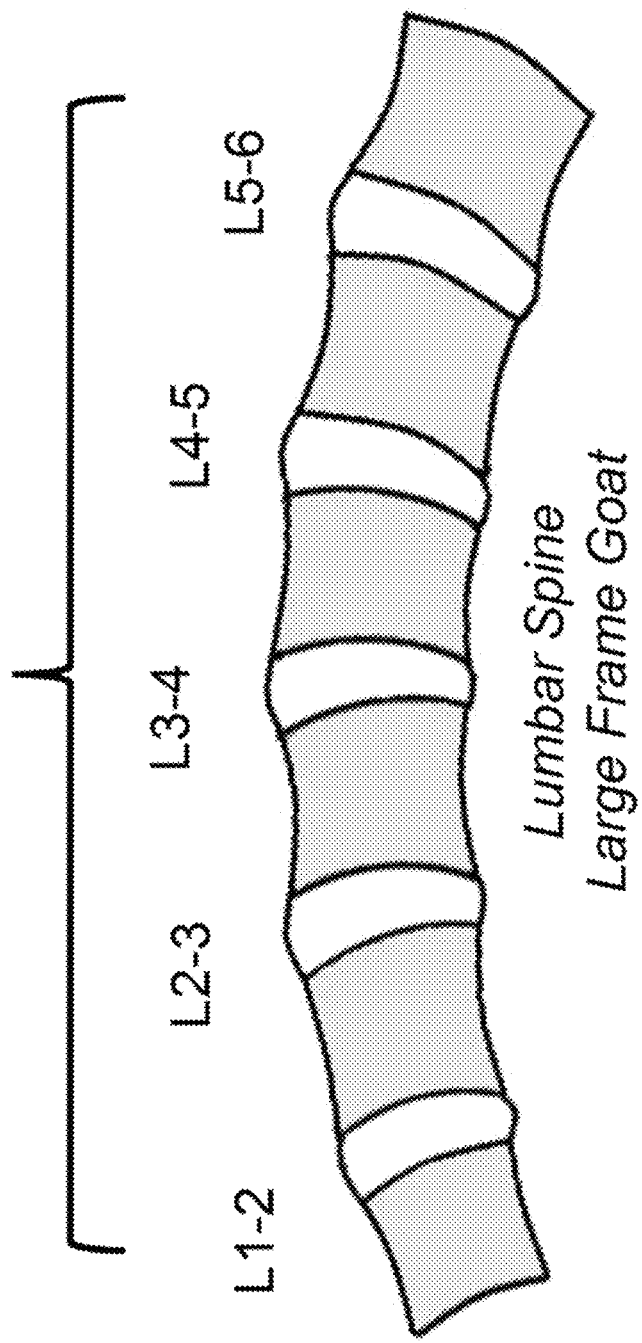
FIG. 3 shows the lumbar spine of a large frame goat and illustrates the study design used in Example 4.

Protocol Summary:

A goat lumbar spine showing the study design is illustrated in FIG. 3. CABC will be injected in three levels of the lumbar spine (L1-2, L2-3 and L4-5) to induce chemonucleolysis and following an induction period, the test article will be administered by surgical implantation into two of the CABC-treated lumbar levels (L2-3 and L4-5). One CABC-treated lumbar level (L1-2) will be a positive control. L3-4 and 5-6 will be negative controls.

Delivery of Test Article:

Following chemonucleolysis, goats will be re-anesthetized and an open, left retroperitoneal transpsoatic approach will be used to access the lumbar spine. Fluoroscopy will be used to identify the treatment levels. The intervertebral disc of the respective lumbar levels will be palpated and a 19 G spinal needle will be advanced into the center of the nucleus pulposus.

Test Article delivery will be performed under fluoroscopic guidance. Volume delivered will be recorded. The test article will be the hydrogel from Example 1A.

Postoperative Procedures:

The goats will recover from anesthesia under close observation by a veterinarian and his/her designee. After recovery, goats will be moved to a dedicated stall and will be released to a barn for the remainder of the study.

Clinical Observations:

Days 1-3 postoperative: The animals will be assessed for postoperative pain and from day 3 to 7 they will be assessed once a day in the morning. All observations will be recorded in individual medical record charts by veterinarians.

Imaging:

Digital Radiography:

Standard ventro-dorsal digital radiographs of the lumbar spine will be obtained in all animals preoperatively and will be used to monitor the status of the indwelling implants postoperative.

Radiographic Exams:

These exams will be done preoperatively for screening purposes, within a few days postoperative and at midterm and end term respectively.

Intra-operative fluoroscopy will be performed for surgical guidance.

Post-Operative MRI:

Postoperative in vivo and/or end term MM

CT:

Computed Tomography may be performed preoperative prior to nucleoplasty. Images will be reconstructed in 3D.

Figure 4:
FIG. 4 shows a radiograph of the lumbar spine of a living goat from the Example 4 after chemonucleolysis using Chondroitinase ABC protease ("C-ABC") and prior to injection of a hydrogel of the present disclosure.

End of Study:

The animals will be sacrificed at two periods and the following postmortem observations will be made:

1) Gross necropsy
2) Macroscopic evaluation
3) MicroCT
4) Histopathology:
5) Test Article Analysis FIG. 4 shows a radiograph of the lumbar spine of a living goat after chemonucleolysis using CABC and prior to injection of the hydrogel of the present disclosure.

Figure 5:
FIG. 5 shows a radiograph indicating the location of two nucleus implants implanted into the intervertebral disc within the lumbar spine of a living goat from the Example 4. The radiograph was taken four days after injection of a hydrogel of the present disclosure. The arrows indicate the location of the implants.

FIG. 5 shows a radiograph indicating the location of two nucleus implants in the lumbar spine of a living goat treated according to the protocol described above. The radiograph was taken four days after injection of a hydrogel of the present disclosure. The arrows indicate the location of the implants. The lateral radiograph indicates that the nucleus implants are well positioned, intact, stable and exhibit a coherent form 4 days after injection of the hydrogel of the present disclosure.

It will be further understood that various changes in the details, materials, and arrangements of the parts which have been described and illustrated in order to explain the nature of this invention may be made by those skilled in the art without departing from the scope of the invention as expressed in the following claims.

Embodiments

1. A hydrogel, comprising:
at least one polymer; and
a solvent, wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa.

2. The hydrogel of embodiment 1, wherein the at least one polymer is selected from the group consisting of polyvinyl alcohol, polyvinylpyrrolidone and polyethylene glycol.

3. The hydrogel of embodiment 2, wherein the hydrogel comprises polyvinyl alcohol, polyvinylpyrrolidone and polyethylene glycol.

4. The hydrogel of embodiment 2, wherein the polyvinyl alcohol has an Mw of between about 60,000 Da to about 190,000 Da.

5. The hydrogel of embodiment 2, wherein the polyethylene glycol has an Mw of about 100 Da to about 4600 Da.

6. The hydrogel of embodiment 2, wherein the polyvinylpyrrolidone has an Mw of about 5,000 Da to about 60,000 Da.

7. The hydrogel of embodiment 1, wherein the solvent is selected from the group consisting of water, dimethylsulfoxide, saline, or a phosphate buffer.

8. The hydrogel of embodiment 1, further comprising a contrast agent.

9. The hydrogel of embodiment 8, wherein the contrast agent is barium sulfate.

10. The hydrogel of embodiment 1, further comprising a dye or colorant.

11. The hydrogel of embodiment 1, wherein the hydrogel is capable of injection at an injection rate of at least 2.5 cc per minute.

12. The hydrogel of embodiment 1, wherein the hydrogel is capable of injection at an injection rate of at least 3.0 cc per minute.

13. The hydrogel of embodiment 1, wherein the tissue is selected from the group consisting of nucleus of an intervertebral disc.

14. The hydrogel of embodiment 18, wherein the tissue is the nucleus of an intervertebral disc.

15. The hydrogel of embodiment 1, wherein the hydrogel has a viscosity of about 10 Pa·s at a temperature of about 65° C.

16. The hydrogel of embodiment 1, wherein the hydrogel is packaged in a syringe.

17. A hydrogel, comprising:
about 12 wt. % to about 22 wt. % of polyvinyl alcohol;
about 0.12 wt. % to about 0.22 wt. % of polyvinylpyrrolidone and;
about 12 wt. % and about 22 wt. % polyethylene glycol; and
a solvent.

18. The hydrogel of embodiment 17, wherein at a temperature of about 65° C. the hydrogel is capable of injection through a 16 cm length, 17 gauge needle at an injection rate of at least 2.0 cc per minute using an injection pressure of about 50 p.s.i. to provide a tissue implant having a mechanical modulus of between about 0.1 to 5.0 MPa.

19. The hydrogel of embodiment 18, wherein the hydrogel is capable of injection at an injection rate of at least 2.5 cc per minute.

20. The hydrogel of embodiment 18, wherein the hydrogel is capable of injection at an injection rate of at least 3.0 cc per minute.

21. The hydrogel of embodiment 17, wherein the hydrogel comprises:
about 17 wt. % of polyvinyl alcohol;
about 0.17 wt. percent of polyvinylpyrrolidone; and
about 16.8 wt. % of polyethylene glycol.

22. The hydrogel of embodiment 17, wherein the polyvinyl alcohol has an Mw of about 60,000 Da to about 190,000 Da;
the polyethylene glycol has an Mw of about 100 Da to about 4600 Da; and the polyvinylpyrrolidone has an Mw of about 5,000 Da to about 60,000 Da.

23. The hydrogel of embodiment 17, wherein the solvent is selected from the group consisting of water, dimethyl sulfoxide, saline, or a phosphate buffer.

24. The hydrogel of embodiment 17, further comprising a contrast agent.

25. The hydrogel of embodiment 24, wherein the contrast agent is barium sulfate.

26. The hydrogel of embodiment 17, further comprising a visualization agent.

27. The hydrogel of embodiment 17, wherein the tissue is selected from the group consisting of the nucleus of an intervertebral disc and the submucosal space under the ureteric orifice.

28. The hydrogel of embodiment 27, wherein the tissue is the nucleus of an intervertebral disc.

29. The hydrogel of embodiment 17, wherein the hydrogel has a viscosity of about 10 Pa·s at a temperature of about 65° C.

30. The hydrogel of embodiment 17, wherein the hydrogel is packaged in a syringe.

31. A tissue implant having a mechanical modulus of between about 0.1 to 5.0 MPa, wherein the tissue implant is formed by the injection of a hydrogel into a living patient's tissue, wherein the hydrogel comprises:
at least one polymer; and a solvent, wherein at a temperature of about 65° C. the hydrogel is capable of injection through a 16 cm length, 17 gauge needle at an injection rate of at least 2.0 cc per minute using an injection pressure of about 50 p.s.i.

32. The tissue implant of embodiment 31, wherein the tissue is the nucleus of an intervertebral disc.

33. A tissue implant having a mechanical modulus of between about 0.1 to 5.0 MPa, wherein the tissue implant is formed by the injection of a hydrogel into a living patient's tissue, wherein the hydrogel comprises:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and a solvent.

34. The tissue implant of embodiment 33, wherein at a temperature of about 65° C. the hydrogel is capable of injection through a 16 cm length, 17 gauge needle at an injection rate of at least 2.0 cc per minute using an injection pressure of about 50 p.s.i.

35. The tissue implant of embodiment 34, wherein the tissue is the nucleus of an intervertebral disc.

36. A method of repairing or supplementing a tissue in a patient in need thereof, comprising:

(a) filling a syringe with a hydrogel comprising at least one polymer and a solvent;
(b) heating the hydrogel of step (a) to about 65° C.;
(c) connecting a 15 gauge or smaller needle to the syringe;
(d) inserting the needle into the tissue in need of repair or supplement; and
(e) injecting a therapeutically effective amount of the hydrogel into the tissue to provide a tissue implant, wherein at a temperature of about 65° C. the hydrogel is capable of injection through a 16 cm length, 17 gauge needle at an injection rate of at least 2.0 cc per minute using an injection pressure of about 50 p.s.i. to provide a tissue implant having a mechanical modulus of between about 0.1 to 5.0 MPa.

37. The method of embodiment 36, wherein the tissue is the nucleus of an intervertebral disc.

38. The method of embodiment 36, wherein the needle is a 17 gauge needle.

39. The method of embodiment 36, wherein the needle is an 18 gauge needle.

40. The method of embodiment 36, wherein the injection rate of the hydrogel into the tissue is at least 2.5 cc per minute.

41. The method of embodiment 36, wherein the injection rate of the hydrogel into the tissue is at least 3.0 cc per minute.

42. The method of embodiment 36, wherein the therapeutically effective amount of the hydrogel is about 1.8 cc.

43. A method of repairing or supplementing a tissue in a patient in need thereof, comprising:
(a) filling a syringe with a hydrogel comprising:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent;
(b) heating the hydrogel of step (a) to about 65° C.;
(c) connecting a 15 gauge or smaller needle to the syringe;
(d) inserting the needle into the tissue in need of repair or supplement; and
(e) injecting a therapeutically effective amount of the hydrogel into the tissue to provide a tissue implant.

44. The method of embodiment 43, wherein at a temperature of about 65° C. the hydrogel is capable of injection through a 16 cm length, 17 gauge needle at an injection rate of at least 2.0 cc per minute using an injection pressure of about 50 p.s.i. to provide a tissue implant having a mechanical modulus of between about 0.1 to 5.0 MPa.

45. The method of embodiment 44, wherein the tissue is the nucleus of an intervertebral disc.

46. The method of embodiment 44, wherein the needle is a 17 gauge needle.

47. The method of embodiment 44, wherein the needle is an 18 gauge needle.

48. The method of embodiment 44, wherein the injection rate of the hydrogel into the tissue is at least 2.5 cc per minute.

49. The method of embodiment 44, wherein the injection rate of the hydrogel into the tissue is at least 3.0 cc per minute.

50. The method of embodiment 43, wherein the tissue implant has a mechanical modulus of between about 0.1 to 1.0 MPa.

51. The method of embodiment 43, wherein the therapeutically effective amount of the hydrogel is about 1.8 cc.

52. A method of manufacturing a hydrogel comprising:
(a) forming a mixture of at least one polymer and a solvent;
(b) stirring the mixture of step (a);
(c) melting the stirred mixture of step (b) to form a solution; and
(d) cooling the solution of step (c) to provide a hydrogel, wherein at a temperature of about 65° C. the hydrogel is capable of injection through a 16 cm length, 17 gauge needle at an injection rate of at least 2.0 cc per minute using an injection pressure of about 50 p.s.i. to provide a tissue implant having a mechanical modulus of between about 0.1 to 5.0 MPa.

53. A method of manufacturing a hydrogel comprising:
about 12 wt. % to about 22 wt. % of polyvinyl alcohol;
about 0.12 wt. percent to about 0.22 wt. % of polyvinylpyrrolidone;
about 12 wt. % and about 22 wt. % polyethylene glycol; and
a solvent, the method comprising:
(a) forming a mixture of polyvinyl alcohol, polyvinylpyrrolidone, polyethylene glycol and a solvent;
(b) stirring the mixture of step (a);
(c) melting the stirred mixture of step (b) to form a solution; and
(d) cooling the solution of step (c).

The invention claimed is:

1. A method of repairing or supplementing the nucleus of an intervertebral disc in a patient in need thereof, comprising:
(a) filling a syringe with a hydrogel comprising:
about 12 wt. % to about 22 wt. % of polyvinyl alcohol;
about 0.12 wt. percent to about 0.22 wt. % of polyvinylpyrrolidone;
about 12 wt. % to about 22 wt. % non-functionalized polyethylene glycol having a Mw of about 500 Da to about 2,000 Da; and
a solvent,
wherein the hydrogel does not contain a chemically cross-linked polymer;
(b) heating the hydrogel of step (a) to about 65° C.;
(c) connecting a 15 gauge or smaller needle to the syringe;
(d) inserting the needle into the nucleus of an intervertebral disc in need of repair or supplement; and
(e) injecting a therapeutically effective amount of the hydrogel, wherein the hydrogel does not contain a chemically cross-linked polymer, into the nucleus of an intervertebral disc to provide a tissue implant.

2. The method of claim 1, wherein at a temperature of about 65° C. the hydrogel is capable of injection through a 16 cm length, 17 gauge needle at an injection rate of at least 1.0 cc per minute using an injection pressure of about 25 p.s.i. to provide a tissue implant having a mechanical modulus of between about 0.1 to 5.0 MPa.

3. The method of claim 1, wherein the needle is a 17 gauge needle.

4. The method of claim 1, wherein the tissue implant has a mechanical modulus of between about 0.1 to 1.0 MPa.

5. The method of claim 1, wherein the therapeutically effective amount of the hydrogel is about 1.8 cc.

6. The method of claim 1, wherein the non-functionalized polyethylene glycol has a Mw of about 900 Da to about 1,100 Da.

7. The method of claim 1, wherein the non-functionalized polyethylene glycol has a Mw of about 1,000 Da.

8. The method of claim 1, further comprising:
removing the nucleus pulposus prior to injecting a therapeutically effective amount of the hydrogel.

9. The method of claim 1, further comprising:

injecting an enzyme into the nucleus of the intervertebral disc to dissolve the nucleus pulposus in need of replacement prior to injecting a therapeutically effective amount of the hydrogel.

10. The method of claim 9, further comprising:

removing the dissolved tissue from the nucleus of the intervertebral disc.

11. The method of claim 9, wherein the enzyme is a serine protease.

12. The method of claim 9, wherein the enzyme is a Chondroitinase enzyme.

13. The method of claim 1, wherein the hydrogel further comprises a contrast agent.

14. The method of claim 13, wherein the contrast agent is barium sulfate.

15. The method of claim 1, wherein the backpressure during the injection is from about 60 p.s.i. to about 200 p.s.i.

16. The method of claim 1, wherein the maximum backpressure during the injection is less than about 200 p.s.i.

* * * * *

UNITED STATES PATENT AND TRADEMARK OFFICE
CERTIFICATE OF CORRECTION

PATENT NO. : 10,507,264 B1
APPLICATION NO. : 16/241510
DATED : December 17, 2019
INVENTOR(S) : Anthony Lowman et al.

Page 1 of 1

It is certified that error appears in the above-identified patent and that said Letters Patent is hereby corrected as shown below:

On the Title Page

Item (72) Inventors:, please add the fourth inventor, Thomas Schaer, Landenberg, PA (US), to the existing list of inventors Signed and Sealed this
Eighth Day of June, 2021

Drew Hirshfeld
*Performing the Functions and Duties of the
Under Secretary of Commerce for Intellectual Property and
Director of the United States Patent and Trademark Office*